US00PP15237P2

(12) United States Plant Patent
Jonkers

(10) Patent No.: US PP15,237 P2
(45) Date of Patent: Oct. 19, 2004

(54) ***IMPATIENS* PLANT NAMED 'FIFY PINK'**

(50) Latin Name: *Impatiens walleriana*
Varietal Denomination: Fify Pink

(75) Inventor: Johanna B. Jonkers, RK Hoorn (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 145 days.

(21) Appl. No.: 10/397,999

(22) Filed: Mar. 25, 2003

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—Michelle Kizilkaya
(74) *Attorney, Agent, or Firm*—Jondle & Associates PC

(57) ABSTRACT

An *impatiens* cultivar particularly distinguished by pink colored flowers, compact habit and good basal branching.

1 Drawing Sheet

Genus and species: *Impatiens walleriana.*
Variety denomination: 'Fify Pink'.

BACKGROUND OF THE NEW PLANT

The present invention comprises a new and distinct cultivar of *impatiens*, botanically known as *Impatiens walleriana,* and hereinafter referred to by the cultivar name 'Fify Pink'. The new cultivar is asexually reproduced from vegetative cuttings and tissue culture resulting from the cross of the seed/pod parent MRO-4-9, a pink proprietary line that is unnamed and unpatented×IW-761-2, a rose proprietary line that is unnamed and unpatented.

'Fify Pink' is a product of a planned breeding program intended to create new *impatiens* plants with pink colored flowers, compact habit, good basal branching and moderately vigorous growth.

The new cultivar was created in 1999 in Andijk, The Netherlands and has been asexually reproduced repeatedly by vegetative cuttings and tissue culture in Gilroy, Calif., Andijk, The Netherlands and Guatemala over a 3-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new *impatiens* plant is illustrated by the accompanying photograph which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Fify Pink'. The data which defines these characteristics were collected from asexual reproductions carried out in Gilroy, Calif. The plant history was taken on 6 month old plants grown in 5-inch pots, in a poly-covered greenhouse under natural light and color readings were taken in the greenhouse. Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.—Impatiens walleriana.*
*Commercial.—Impatiens.*
Form: Compact, small mounded.
Growth and branching habit: Compact habit, good basal branching, moderately vigorous, pinching of the terminal apices enhances branching.
Height: From soil level to top of blooms: Approximately 8–12 cm.
Width: Approximately 20–30 cm including flowers.
Time to produce a finished flowering plant: 8–10 weeks for a 4-inch pot.
Outdoor plant performance: Shade, free-flowering all year, some heat tolerance. Mixed containers, window boxes and mass plantings.
Time to initiate and develop roots: Approximately 10–21 days in the greenhouse.
Root description: Fibrous, fleshy, white.

THE LEAVES

Arrangement: Alternate.
Length: 3.0–3.6 cm.
Width: 1.9–2.4 cm.
Leaf blade shape: Ovate.
Leaf margin: Crenate with ciliate (1) between each lobe.
Apex aspect: Cuspidate with one ciliate at the tip.
Base aspect: Acuminate.
Foliage color: Upper side, RHS 137A (green) but darker; Underside, RHS 147B (yellow-green) with 137B (green) veining.
Texture: Glabrous.
Venation: Pinnate.
Venation color: RHS 145C (green), fading into the leaf until almost disappears.
Petiole length: 1.0–1.7 cm.
Petiole diameter: 0.20 cm.

Petiole color: RHS 145C (green) with very thin streaks of anthocyanin on some leaves.
Petiole texture: Glabrous.

THE STEM

Length: 10–15 cm.
Diameter: 0.3–0.4 cm.
Internode length: 0.1–0.4 cm.
Color: RHS 144A (yellow-green) but a little lighter.
Texture: Glabrous.
Stem anthocyanin: Yes, in irregular small blotches.
Pedicel diameter: 0.1 cm.
Pedicel length: 1.3–2.3 cm.
Pedicel color: RHS 144A (yellow-green) little lighter.
Pedicel texture: Glabrous.
Peduncle length: 1.7–2.1 cm.
Peduncle diameter: 0.15 cm.
Peduncle color: RHS 144A (yellow-green) but little lighter.
Peduncle texture: Glabrous.

THE BUD

Shape: Ovate.
Diameter: 0.4 cm.
Length: 0.5–0.7 cm.
Color at tight bud: RHS 65C (red-purple) with blush at RHS 63B (red-purple) in irregular intensities.

THE FLOWER

Blooming habit: Continuous and freely all through the year.
Inflorescence type: Racemes in leaf axis.
Number of flowers per raceme and/or whorl: 10–20 including buds.
Number of petals and floret form: 5; 1 standard or dorsal (free), 2 lateral or lobed pairs (wing petals) deeply lobed.
Flower color: Dorsal petal is RHS 65A (red-purple) base color with RHS N66A and B (red-purple) blushing in light intensities in vein like pattern, and heavily basally at the ovary. Lateral petals are RHS 68B (red-purple) base color with RHS N66B (red-purple) blush, basally at the ovary.
Flower color: Underside, dorsal is RHS 73D (red-purple) with a blush of RHS 71C (red-purple) but lighter and irregular amounts and intensities and a keel of RHS 145B (yellow-green). Lateral petals are RHS 73D (red-purple).
Floret diameter: 2.3–2.5 cm.
Floret height: 2.5–2.7 cm.
Petal size, dorsal: length 0.7–0.9 cm; width 1.0–1.1 cm; shape orbicular; apex shape retuse. Lateral petal: length 1.3–1.4 cm; width 0.7–0.8 cm; shape obovate; apex shape retuse.
Petal base shape: Fused.
Petal margin: Entire.
Petal texture: Papillose.
Sepals: Three, one larger than the others with a spur.
Large sepal: Color is RHS 155B (white) somewhat translucent with a slight greenish hue to the tip; length 0.5 cm; width 0.3–0.35 cm; shape ovate; apex shape cuspidate; base shape fused; spur color is RHS 37D (red) with an indeterminate green hue intermingled, with RHS 145C (yellow-green) tip, at approximately the last 0.2 cm; length 2.5–2.6 cm.
Small sepal: Color is RHS 144A (yellow-green); at the tips and a little lighter basally; length 0.2 cm; width 0.1 cm; shape ovate; apex shape acute; base shape fused.
Sepal texture: Glabrous.
Lastingness of individual blooms: 4–8 days.
Fragrance: No.

THE REPRODUCTIVE ORGANS

Stamens: Five more or less fused by the anthers and covering the ovary; color is RHS 61C (red-purple) (pollen cap).
Pollen amount and color: Not observed.
Pistil: One, complete.
Fruit seed set: Not observed.

DISEASE AND INSECT RESISTANCE

Not observed.

COMPARISON WITH KNOWN CULTIVARS

'Fify Pink Two' differs from the female parents in the following ways: Male and female has a normal sized flower and habit. The male flower is rose while the 'Fify Pink Two' is pink.

I claim:

1. A new and distinct cultivar of *impatiens* plant as shown and described herein.

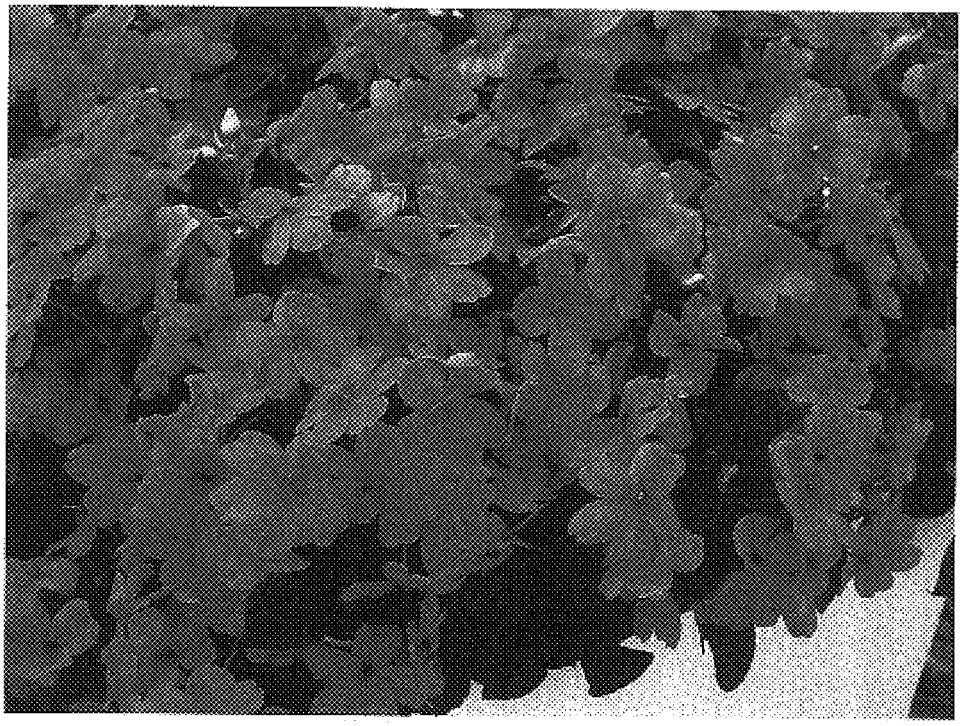

* * * * *